United States Patent [19]
Anderson

[11] Patent Number: 5,970,992
[45] Date of Patent: Oct. 26, 1999

[54] DENTAL FLOSSING DEVICE

[76] Inventor: Sherlie A. Anderson, 3213 Capehart Dr., St Louis, Mo. 63121-5320

[21] Appl. No.: 09/220,918

[22] Filed: Dec. 24, 1998

[51] Int. Cl.⁶ .................................................. A61C 15/04
[52] U.S. Cl. ............................................................ 132/323
[58] Field of Search .................................. 132/323, 324, 132/321, 325, 326, 327, 329

[56] References Cited

U.S. PATENT DOCUMENTS

| | | | |
|---|---|---|---|
| 788,947 | 5/1905 | Roth | 132/323 |
| 1,287,926 | 12/1918 | Ecaubert | 132/326 |
| 1,533,664 | 4/1925 | Sanford | 132/323 |
| 2,180,522 | 11/1939 | Henne | 132/323 |
| 2,443,415 | 6/1948 | Buscarino | 132/323 |
| 2,702,555 | 2/1955 | De Mar | 132/323 |
| 4,531,530 | 7/1985 | Aiken | 132/323 |

FOREIGN PATENT DOCUMENTS

| | | | |
|---|---|---|---|
| 2842404 | 4/1980 | Germany | 132/323 |

*Primary Examiner*—Todd E. Manahan
*Assistant Examiner*—Eduardo C. Robert

[57] ABSTRACT

A dental flossing device for removing food and debris from between teeth and crowns. The dental flossing device includes an elongate arcuate bow member with opposite first and second ends. A pair of floss loops are linked together and each floss loop is coupled to an end of the bow member. Each of the floss loops may extend into an aperture of the respective end of the bow member and be coupled in the apertures. Alternatively, each of the ends of the bow member has a pair of finger portions forming a channel between them. First and second floss loops extend between the first and second ends of the bow member. Each of the floss loops comprises a length of dental floss. The length of dental floss of the first floss loop extends through the second floss loop such that the floss loops are linked together. The first floss loop extends through the channel of the first end of the bow member. The second floss loop extends through the channel of the second end of the bow member.

19 Claims, 3 Drawing Sheets

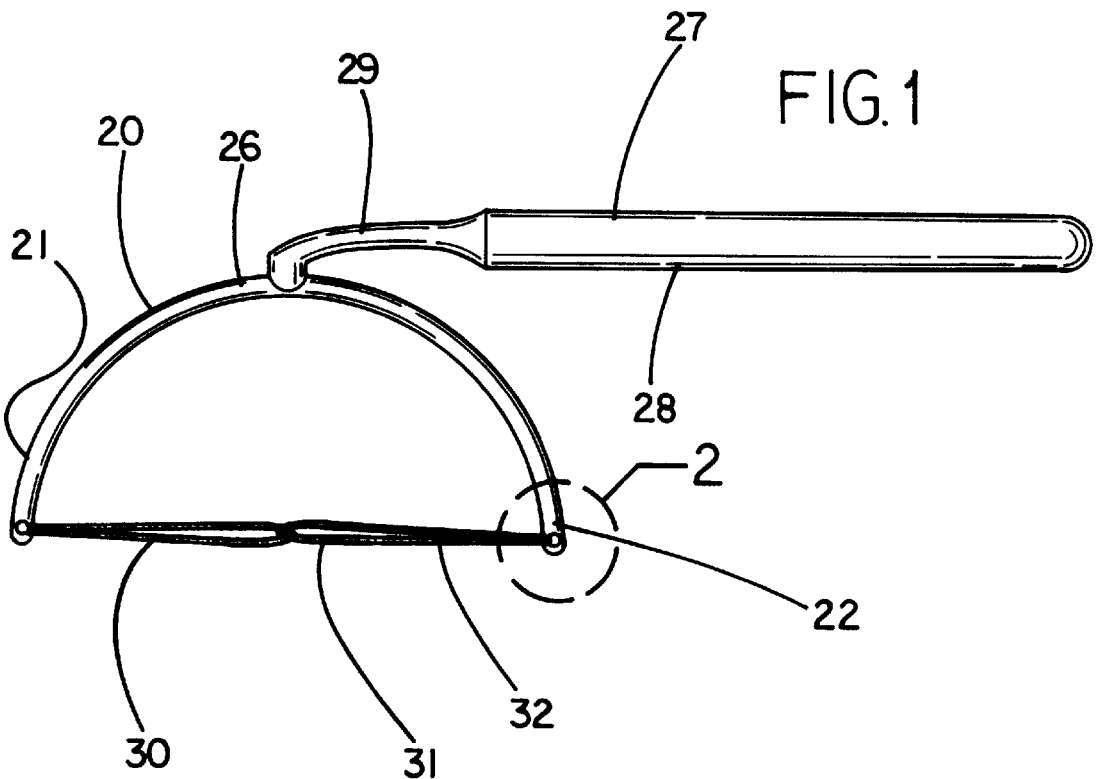
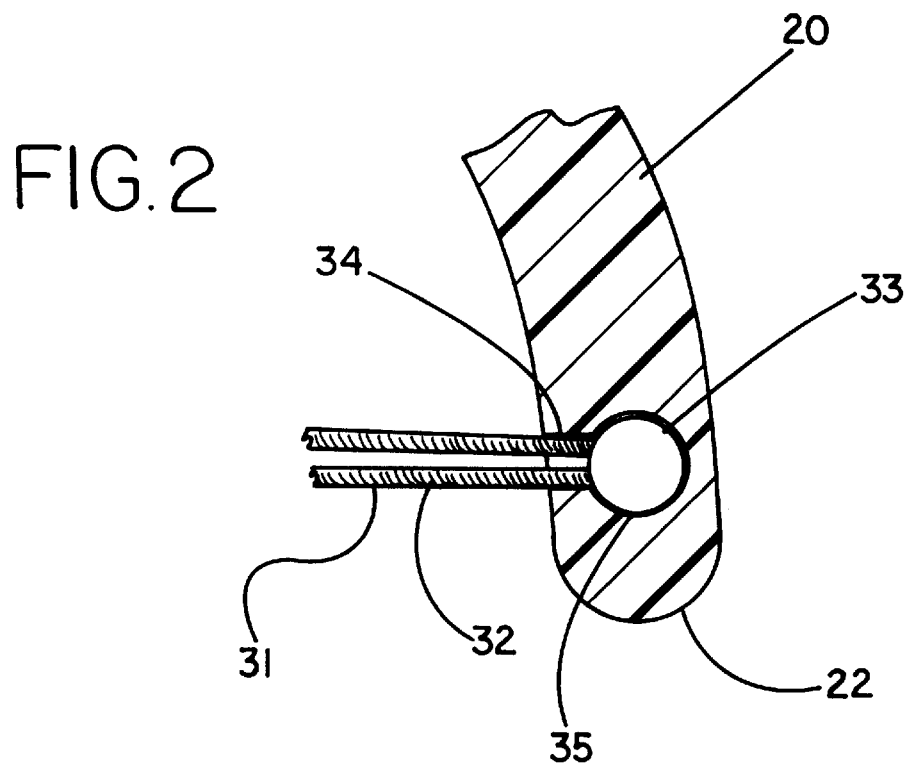

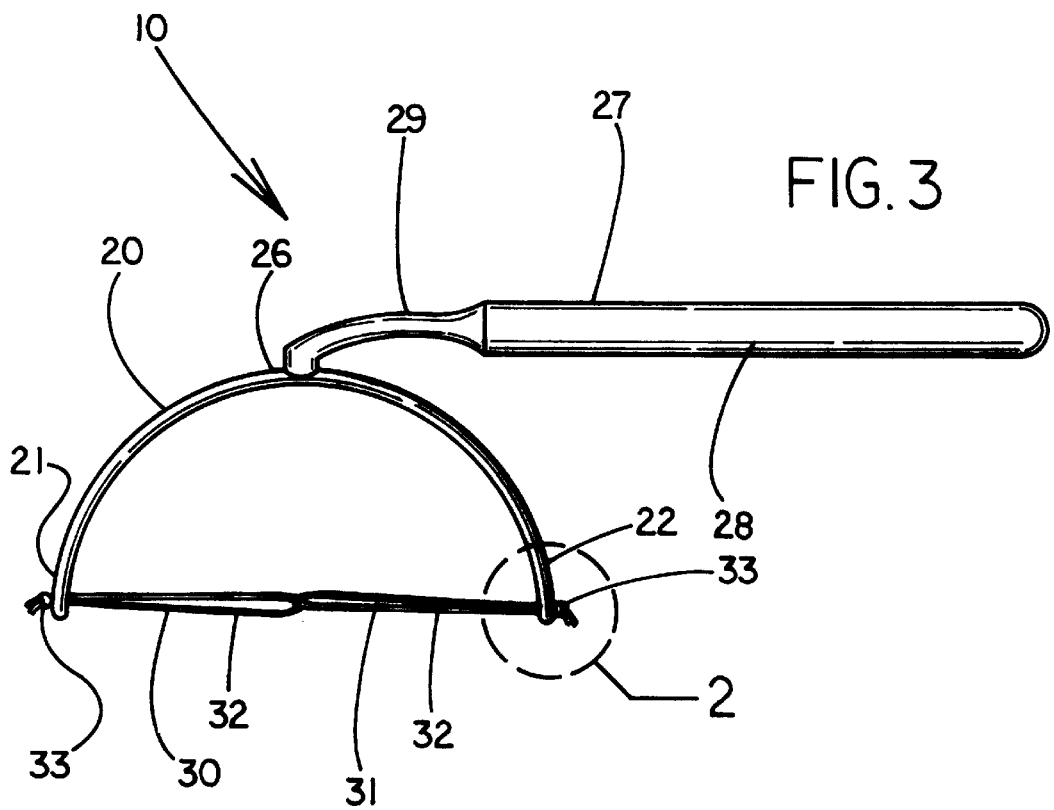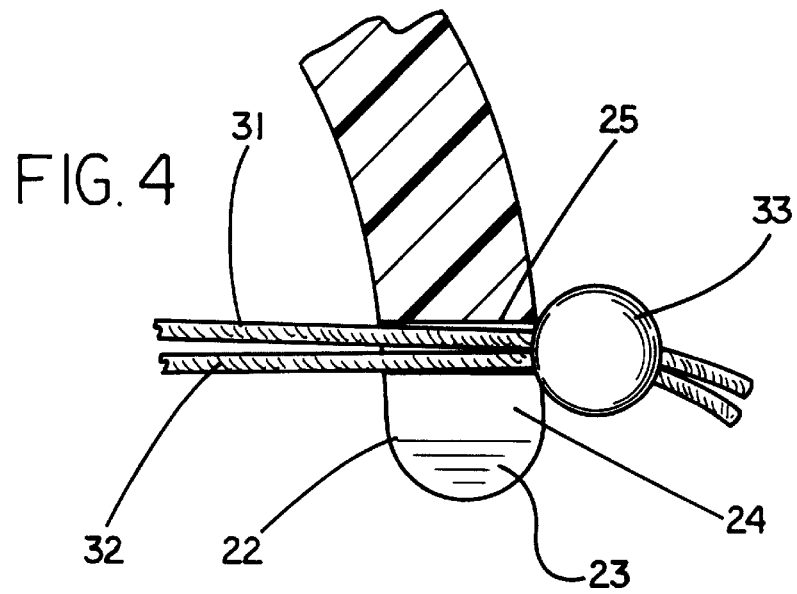

DENTAL FLOSSING DEVICE

BACKGROUND OF THE INVENTION

1. Field of the Invention

The present invention relates to floss holders and more particularly pertains to a new dental flossing device for removing food and debris from between teeth and crowns.

2. Description of the Prior Art

The use of floss holders is known in the prior art. More specifically, floss holders heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 2,354,454; U.S. Pat. No. 2,650,598; U.S. Pat. No. 2,059,287; U.S. Pat. No. 3,631,869; U.S. Pat. No. 5,483,982; and U.S. Pat. No. Des. 268,955.

While these devices fulfill their respective, particular objectives and requirements, the aforementioned patents do not disclose a new dental flossing device. The inventive device includes an elongate arcuate bow member with opposite first and second ends. First and second floss loops extend between the first and second ends of the bow member. The first floss loop extends through the second floss loop such that the floss loops are linked together. The first floss loop is coupled to the first end of the bow member. The second floss loop is coupled to the second end of the bow member.

In these respects, the dental flossing device according to the present invention substantially departs from the conventional concepts and designs of the prior art, and in so doing provides an apparatus primarily developed for the purpose of removing food and debris from between teeth and crowns.

SUMMARY OF THE INVENTION

In view of the foregoing disadvantages inherent in the known types of floss holders now present in the prior art, the present invention provides a new dental flossing device construction wherein the same can be utilized for removing food and debris from between teeth and crowns.

The general purpose of the present invention, which will be described subsequently in greater detail, is to provide a new dental flossing device apparatus and method which has many of the advantages of the floss holders mentioned heretofore and many novel features that result in a new dental flossing device which is not anticipated, rendered obvious, suggested, or even implied by any of the prior art floss holders, either alone or in any combination thereof.

To attain this, the present invention generally comprises an elongate arcuate bow member with opposite first and second ends. Each of the ends of the bow member has a pair of finger portions forming a channel between them. First and second floss loops extend between the first and second ends of the bow member. Each of the floss loops comprises a length of dental floss. The length of dental floss of the first floss loop extends through the second floss loop such that the floss loops are linked together. The first floss loop extends through the channel of the first end of the bow member. The second floss loop extends through the channel of the second end of the bow member.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new dental flossing device apparatus and method which has many of the advantages of the floss holders mentioned heretofore and many novel features that result in a new dental flossing device which is not anticipated, rendered obvious, suggested, or even implied by any of the prior art floss holders, either alone or in any combination thereof.

It is another object of the present invention to provide a new dental flossing device which may be easily and efficiently manufactured and marketed.

It is a further object of the present invention to provide a new dental flossing device which is of a durable and reliable construction.

An even further object of the present invention is to provide a new dental flossing device which is susceptible of a low cost of manufacture with regard to both materials and labor, and which accordingly is then susceptible of low prices of sale to the consuming public, thereby making such dental flossing device economically available to the buying public.

Still yet another object of the present invention is to provide a new dental flossing device which provides in the apparatuses and methods of the prior art some of the advantages thereof, while simultaneously overcoming some of the disadvantages normally associated therewith.

Still another object of the present invention is to provide a new dental flossing device for removing food and debris from between teeth and crowns.

Yet another object of the present invention is to provide a new dental flossing device which includes an elongate arcuate bow member with opposite first and second ends. Each of the ends of the bow member has a pair of finger portions forming a channel between them. First and second floss loops extend between the first and second ends of the bow member. Each of the floss loops comprises a length of dental floss. The length of dental floss of the first floss loop extends through the second floss loop such that the floss loops are linked together. The first floss loop extends through the channel of the first end of the bow member. The second floss loop extends through the channel of the second end of the bow member.

Still yet another object of the present invention is to provide a new dental flossing device that permits flossing with one hand.

Even still another object of the present invention is to provide a new dental flossing device that utilizes two pieces of floss to provide more flossing surface.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a schematic side view of a new dental flossing device according to the present invention.

FIG. 2 is a schematic detailed partial cross-sectional view of the present invention taken from Circle 2 of FIG. 1.

FIG. 3 is a schematic side view of a new dental flossing device according to the present invention.

FIG. 4 is a schematic detailed partial cross-sectional view of the present invention taken from Circle 4 of FIG. 3.

DESCRIPTION OF THE PREFERRED EMBODIMENT

Figure 5:
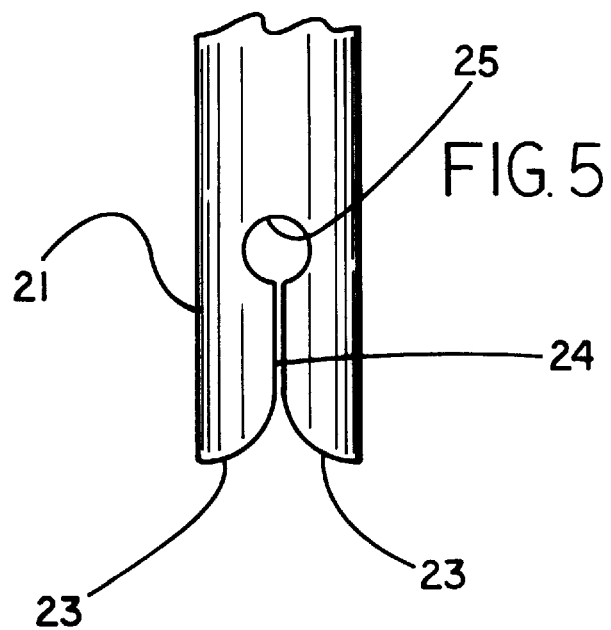
FIG. 5 is a schematic detailed side view of the present invention.
Figure 6:
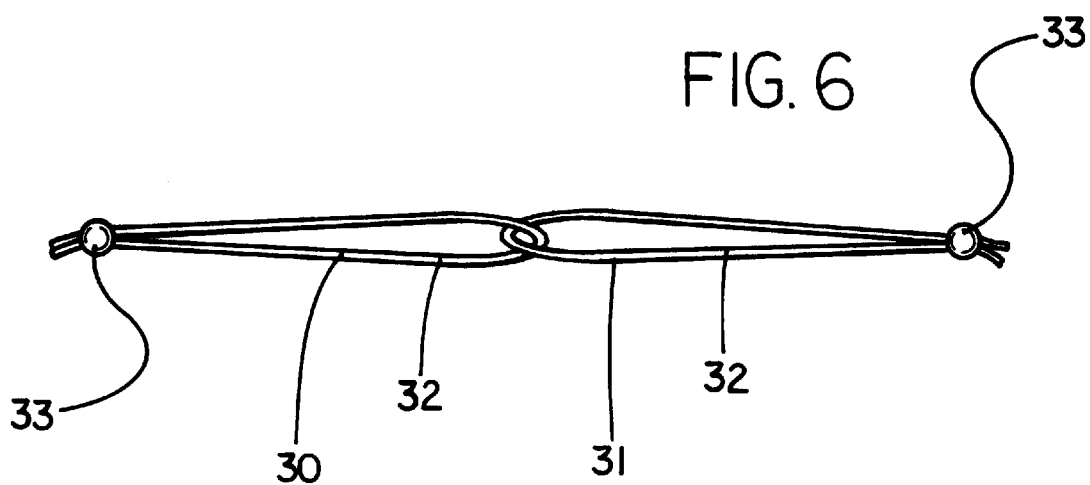
FIG. 6 is a schematic side view of the floss strips of the present invention.

With reference now to the drawings, and in particular to FIGS. 1 through 6 thereof, a new dental flossing device embodying the principles and concepts of the present invention and generally designated by the reference numeral 10 will be described.

As best illustrated in FIGS. 1 through 6, the dental flossing device 10 generally comprises an elongate arcuate bow member 20 with opposite first and second ends 21,22. First and second floss loops 30,31 are linked together. The first floss loop 30 is coupled to said first end 21 of the bow member 20. The second floss loop 31 is coupled to the second end 22 of said bow member 20.

Preferably, each of the ends of the bow member 20 has an aperture 34 extending into it. Each of the floss loops 30,31 comprises a length of dental floss having opposite ends. The ends of the lengths of dental floss 32 extend into the apertures 34 of the ends of the bow member 20 and are coupled to the bow member 20 in the apertures 34. Ideally, each of the floss loops further comprises a coupling bead 33 to couple the ends of each of the floss loops to the bow member. Each of the coupling beads 33 couples the ends of a respective length of dental floss together. The coupling beads 33 are disposed in cavities 35 of the ends of the bow member to help prevent the ends of the lengths of dental floss of the floss loops from slipping through the apertures 34 of the ends of the bow member.

Alternatively, each of the ends of the bow member 20 has a pair of finger portions 23 forming a channel 24 between them. First and second floss loops 30,31 extend between the first and second ends 21,22 of the bow member 20. Each of the floss loops 30,31 comprises a length of dental floss 32. The length of dental floss 32 of the first floss loop 30 extends through the second floss loop 31 such that the floss loops 30,31 are linked together. The first floss loop 30 extends through the channel 24 of the first end 21 of the bow member 20. The second floss loop 31 extends through the channel 24 of the second end 22 of the bow member 20.

Preferably, as shown in FIG. 3, each of the finger portions 23 of the ends 21,22 of the bow member 20 taper away from the channel 24 for facilitating insertion of dental floss into the channel 24.

Also preferably, each of the floss loops 30,31 comprises a length of dental floss 32 that has opposite ends. As best shown in FIG. 4, the length of dental floss 32 of the first floss loop 30 extends through the second floss loop 31 such that the floss loops 30,31 are linked together. As illustrated in FIGS. 1 and 2, the ends of the first floss loop 30 are extended through the channel 24 of the first end 21 of the bow member 20 while the ends of the second floss loop 31 are extended through the channel 24 of the second end 22 of the bow member 20. Ideally, the floss loops 30,31 are stretched tight between the ends 21,22 of the bow member 20 such that the ends of the bow member 20 are flexed together when the floss loops are attached to them.

Preferably, an innermost portion of each of the channels 24 has a generally circular floss receiving portion 25 designed for receiving dental floss therebetween. As shown in FIGS. 1 and 2, the ends of the first floss loop 30 extend through the floss receiving portion 25 of the channel 24 of the first end 21 of the bow member 20. The ends of the second floss loop 31 extend through the floss receiving portion 25 of the channel 24 of the second end 22 of the bow member 20.

Also preferably, each of the floss loops 30,31 further comprises a coupling bead 33. The coupling bead 33 couples the ends of each of the lengths of dental floss 32 together. The coupling beads 33 abut the ends of the bow member 20, as shown in FIG. 2, to help prevent the ends of the lengths of dental floss 32 of the floss loops 30,31 from slipping through the channels 24 of the ends of the bow member 20. More preferably, the diameter of each of the coupling beads 33 is greater than an inner diameter of each of the floss receiving portions 25 of the channels 24 of the ends of the bow member 20 to help prevent the floss loops 30,31 from slipping out of the floss receiving portions 25. Most ideally, each of the coupling beads 33 is generally spherical such that they enter slightly into the floss receiving portions 25 and are held there by tensile pressure so that the floss loops 30,31 don't slide out of the floss receiving portions 25 and back into the channels 24.

Preferably, the bow member 20 has a center region 26 that is generally positioned between the first and second ends 21,22 of the bow member 20. A handle 27 member extends from the center region 26 of the bow member 20. Ideally, the handle 27 has a generally cylindrical grasping portion 28 and an arcuate neck portion 29 extending between the grasping portion 28 and the bow member 20.

Preferably, the bow member 20 generally follows an imaginary circle has a radius of between about ½ and 2 inches, ideally about 1 inch. Also preferably, the radial distance between the first and second ends 21,22 of the bow member 20 is between about 160 and 200 degrees, ideally about 180 degrees. Also preferably, the bow member 20 has a generally cylindrical transverse cross-section, the cross-section of the bow member 20 has an outer diameter of between about 1/16 and 1/3 inch, ideally about 1/8 inch.

A length of each of the lengths of dental floss 32 is defined between the ends of the length of dental floss 32. Preferably, the lengths of each of the lengths of dental floss 32 is about equal. More preferably, the lengths of each of the lengths of dental floss 32 is between about ½ and 4½ inches, ideally about 1 inch.

In use, the floss loops 30,31 are placed between the teeth or crown area and moved back and forth in a sawing motion until food and debris are dislodged from the area. The floss loops 30,31 are pulled up and out in a sweeping motion to remove food and debris from the sides of teeth. Remove food particles and debris from the floss loops 30,31 by holding under running water and repeat the above procedure until all food is gone. To replace the floss loops 30,31, the ends of the floss loops 30,31 are pulled outwardly along the fingers of the bow member 20 and out of the channels 24. New floss loops 30,31 are placed between the tapered portions of the fingers and slipped through the channel 24 into the floss receiving portions 25 of the channels 24.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A flossing device, comprising:
   an elongate arcuate bow member having opposite first and second ends;
   first and second floss loops, said first floss loop being extended through said second floss loop such that said floss loops are linked together, said first floss loop being coupled to said first end of said bow member, said second floss loop being coupled to said second end of said bow member; and
   wherein each of said ends of said bow member has an aperture extending therein, each of said floss loops comprising a length of dental floss having opposite ends, said ends of said lengths of dental floss extending into said apertures of said ends of said bow member and coupled to said bow member therein.

2. The flossing device of claim 1, each of said floss loops further comprises a coupling bead, each of said coupling beads coupling said ends of a respective length of dental floss together, said coupling beads being disposed in cavities of said ends of said bow member for helping prevent said ends of said lengths of dental floss of said floss loops from slipping through said apertures of said ends of said bow member.

3. The flossing device of claim 1, wherein each of said ends of said bow member has a pair of finger portions forming a channel therebetween, said first floss loop being extended through said channel of said first end of said bow member, said second floss loop being extended through channel of said second end of said bow member.

4. The flossing device of claim 3, wherein each of said finger portions of said ends of said bow member taper away from said channel.

5. The flossing device of claim 3, wherein an innermost portion of each of said channels has a generally circular floss receiving portion designed for receiving dental floss therebetween, said first floss loop being extended through said floss receiving portion of said channel of said first end of said bow member, said second floss loop being extended through said floss receiving portion of said channel of said second end of said bow member.

6. The flossing device of claim 3, wherein each of said lengths of dental floss of said floss loops has opposite ends, said ends of said first floss loop being extended through channel of said first end of said bow member, said ends of said second floss loop being extended through said channel of said second end of said bow member.

7. The flossing device of claim 6 wherein each of said floss loops further comprises a coupling bead, said coupling bead coupling said ends of said length of dental floss together, said coupling beads abutting said ends of said bow member for helping prevent said ends of said lengths of dental floss of said floss loops from slipping through said channels of said ends of said bow member.

8. The flossing device of claim 7, wherein each of said floss loops comprises a length of dental floss having opposite ends, said ends of said first floss loop extending through said floss receiving portion of said channel of said first end of said bow member, said ends of said second floss loop being extended through said floss receiving portion of said channel of said second end of said bow member, wherein the diameter of each of said coupling beads is greater than an inner diameter of each of said floss receiving portions of said channels of said ends of said bow member.

9. The flossing device of claim 7, wherein said coupling beads are generally spherical.

10. The flossing device of claim 1, wherein said bow member has a center region being generally positioned between said first and second ends, a handle member being extended from said center region of said bow member.

11. The flossing device of claim 10, wherein said handle member extends along a plane extending through said handle member.

12. The flossing device of claim 11, wherein the radial distance between said first and second ends of said bow member is between about 160 and 200 degrees.

13. The flossing device of claim 1, wherein said bow member generally follows an imaginary circle having a radius of between about ¼ and 2 inches.

14. The flossing device of claim 1, wherein said bow member has a generally cylindrical transverse cross-section, said cross-section of said bow member having an outer diameter of between about 1/16 and 1/3 inch.

15. The flossing device of claim 1, wherein a length of each of said lengths of dental floss is defined between said ends of said length of dental floss, said lengths of each of said lengths of dental floss being about equal.

16. The flossing device of claim 15, wherein the lengths of each of said lengths of dental floss is between about ½ and 4½ inches.

17. A flossing device, comprising:

an elongate arcuate bow member having opposite first and second ends;

first and second floss loops, said first floss loop being extended through said second floss loop such that said floss loops are linked together, said first floss loop being coupled to said first end of said bow member, said second floss loop being coupled to said second end of said bow member; and wherein each of said ends of said bow member has a pair of finger portions forming a channel therebetween, said first floss loop being extended through said channel of said first end of said bow member, said second floss loop being extended through said channel of said second end of said bow member.

18. The flossing device of claim 17, wherein each of said ends of said bow member has an aperture extending therein, each of said floss loops comprising a length of dental floss having opposite ends, said ends of said lengths of dental floss extending into said apertures of said ends of said bow member and coupled to said bow member therein.

19. A flossing device, comprising:

an elongate arcuate bow member having opposite first and second ends;

each of said ends of said bow member having a pair of finger portions forming a channel therebetween, each of said finger portions of said ends of said bow member tapering away from said channel;

first and second floss loops, each of said floss loops comprising a length of dental floss having opposite ends, said length of dental floss of said first floss loop being extended through said second floss loop such that said floss loops are linked together, said ends of said first floss loop being extended through said channel of said first end of said bow member, said ends of said second floss loop being extended through said channel of said second end of said bow member;

wherein an innermost portion of each of said channels has a generally circular floss receiving portion designed for receiving dental floss therebetween, said ends of said first floss loop being extended through said floss receiving portion of said channel of said first end of said bow member, said ends of said second floss loop being extended through said floss receiving portion of said channel of said second end of said bow member;

each of said floss loops further comprising a coupling bead, said coupling bead coupling said ends of said length of dental floss together, said coupling beads abutting said ends of said bow member for helping prevent said ends of said lengths of dental floss of said floss loops from slipping through said channels of said ends of said bow member;

wherein the diameter of each of said coupling beads is greater than an inner diameter of each of said floss receiving portions of said channels of said ends of said bow member;

said coupling beads being generally spherical;

said bow member having a center region being generally positioned between said first and second ends;

a handle member being extended from said center region of said bow member along a plane extending through said bow member;

wherein said bow member generally follows an imaginary circle having a radius of about ½ inch, wherein the radial distance between said first and second ends of said bow member is about 180 degrees;

wherein said bow member has a generally cylindrical transverse cross-section, said cross-section of said bow member having an outer diameter of about ⅛ inch;

wherein a length of each of said lengths of dental floss is defined between said ends of said length of dental floss, said lengths of each of said lengths of dental floss being about equal; and wherein the lengths of each of said lengths of dental floss is about 1 inch.

* * * * *